(12) United States Patent
Zuidervaart et al.

(10) Patent No.: US 10,857,372 B2
(45) Date of Patent: Dec. 8, 2020

(54) DEVICE FOR TREATING SKIN USING NON-THERMAL PLASMA

(71) Applicant: KONINKLIJKE PHILIPS N.V., Eindhoven (NL)

(72) Inventors: Jasper Zuidervaart, Eindhoven (NL); Eduard Antonius Van Der Zwan, Eindhoven (NL); Stephan Mooibroek, Eindhoven (NL); Jeroen Christian Nijdam, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 199 days.

(21) Appl. No.: 15/574,675

(22) PCT Filed: May 19, 2016

(86) PCT No.: PCT/EP2016/061178
§ 371 (c)(1),
(2) Date: Nov. 16, 2017

(87) PCT Pub. No.: WO2016/192997
PCT Pub. Date: Dec. 8, 2016

(65) Prior Publication Data
US 2018/0133496 A1    May 17, 2018

(30) Foreign Application Priority Data
May 29, 2015  (EP) .................................... 15169883

(51) Int. Cl.
*A61N 1/44* (2006.01)
*H05H 1/24* (2006.01)

(52) U.S. Cl.
CPC ............. *A61N 1/44* (2013.01); *H05H 1/2406* (2013.01); *H05H 2001/2412* (2013.01);
(Continued)

(58) Field of Classification Search
CPC .................. A61N 1/44; H05H 1/2406; H05H 2001/2412; H05H 2240/20;
(Continued)

(56) References Cited

U.S. PATENT DOCUMENTS 4,551,141 A * 11/1985 McNeil ............... A61M 1/0019
604/317
8,267,884 B1 * 9/2012 Hicks ................... A61B 18/042
604/23

(Continued)

FOREIGN PATENT DOCUMENTS

DE    102009002278 A1    10/2010
WO    2007031250 A1    3/2007
(Continued)

*Primary Examiner* — Kevin C Sirmons
*Assistant Examiner* — Tezita Z Watts (57) ABSTRACT

The present application relates to a device for treating skin using non-thermal plasma. It comprises a housing having a skin interface electrode for application to skin during treatment, a generator for generating non-thermal plasma at the skin interface electrode; and an isolating element to isolate a region surrounding said skin interface electrode other than during treatment so that non-thermal plasma generated at the skin interface electrode within said region sterilises the skin interface electrode.

18 Claims, 10 Drawing Sheets

(52) U.S. Cl.
CPC ... *H05H 2240/20* (2013.01); *H05H 2245/122* (2013.01); *H05H 2245/123* (2013.01); *H05H 2245/125* (2013.01); *H05H 2245/1225* (2013.01)

(58) Field of Classification Search
CPC ..... H05H 2240/112; H05H 2240/1225; H05H 1/46; A61L 2/14; A61B 18/042
See application file for complete search history.

(56) References Cited

U.S. PATENT DOCUMENTS

| | | | | |
|---|---|---|---|---|
| 8,328,982 | B1* | 12/2012 | Babayan | C23F 4/00 156/345.43 |
| 8,557,187 | B2* | 10/2013 | Ehlbeck | H01J 37/32541 422/130 |
| 9,656,095 | B2* | 5/2017 | Watson | A61N 1/44 |
| 2006/0156983 | A1* | 7/2006 | Penelon | C23F 4/00 118/723 E |
| 2008/0108951 | A1* | 5/2008 | Jerde | A61M 5/002 604/198 |
| 2009/0012589 | A1* | 1/2009 | Watson | H05H 1/46 607/99 |
| 2009/0277024 | A1* | 11/2009 | Sinnema | B26B 19/40 30/538 |
| 2010/0029275 | A1 | 2/2010 | Bosch | |
| 2010/0145253 | A1* | 6/2010 | Gutsol | A61B 18/042 604/20 |
| 2011/0121735 | A1 | 5/2011 | Penny | |
| 2012/0046602 | A1* | 2/2012 | Morfill | A61M 35/00 604/23 |
| 2012/0187841 | A1* | 7/2012 | Kindel | A61B 18/042 315/111.21 |
| 2012/0259270 | A1* | 10/2012 | Wandke | H05H 1/2406 604/23 |
| 2012/0271225 | A1* | 10/2012 | Stieber | A61B 18/042 604/26 |
| 2012/0288934 | A1* | 11/2012 | Weltmann | C12M 35/02 435/375 |
| 2013/0022514 | A1* | 1/2013 | Morfill | H05H 1/2406 422/186.21 |
| 2013/0291794 | A1* | 11/2013 | Sanematsu | H05H 1/2406 118/688 |
| 2013/0319460 | A1 | 12/2013 | Schneider | |
| 2013/0345620 | A1* | 12/2013 | Zemel | A61B 18/042 604/24 |
| 2016/0242269 | A1* | 8/2016 | Dirk | H05H 1/2406 |

FOREIGN PATENT DOCUMENTS

| | | |
|---|---|---|
| WO | 2011144344 A2 | 11/2011 |
| WO | 2013138449 A1 | 9/2013 |
| WO | 2013144627 A1 | 10/2013 |

* cited by examiner

DEVICE FOR TREATING SKIN USING NON-THERMAL PLASMA

This application is the U.S. National Phase application under 35 U.S.C. § 371 of International Application No. PCT/EP2016/061178, filed on May 19, 2016, which claims the benefit of International Application No. 15169883.4 filed on May 29, 2015. These applications are hereby incorporated by reference herein.

FIELD OF THE INVENTION

The present invention relates to a device for treating skin using non-thermal plasma. The present invention also relates to a method for sterilising a skin interface electrode of a device for treating skin using non-thermal plasma.

BACKGROUND OF THE INVENTION

Plasma is usually defined as an overall electrically neutral gas containing unbound positive and negative particles, such as ions and electrons, and is in particular well-known for its sterilising properties. When such a gas exists at a very high temperature in a stable state, i.e. a state in which ions and electrons are in thermal equilibrium with each other, it is called thermal plasma (or "hot plasma"). Non-thermal plasma (also known as "cold plasma", "low-temperature plasma" or "non-equilibrium plasma") may also exist, in which ions are at a much lower temperature than free electrons, e.g. human body temperature. Non-thermal plasma is therefore suitable for use in many applications such as removal of contaminants from a human body surface, without causing significant thermal tissue damage.

Devices for treating skin using non-thermal plasma are known, for example from WO 2011/144344 A2. Such devices usually comprise a non-thermal plasma source comprising a pair of electrodes and a high voltage power supply. One of the electrodes is located at a skin interface area of the device. To generate non-thermal plasma, a high voltage is applied between the electrodes by the power supply so that electrical discharges occur between the electrodes. Such electrical discharges ionize air located between the electrodes, thereby generating non-thermal plasma. To treat skin, for example to disinfect a wound, the skin interface area of the device is placed in contact with or close to the wound. Then, the non-thermal plasma source is activated to generate non-thermal plasma at the skin interface area. Non-thermal plasma diffuses onto the wound, thereby disinfecting the wound.

Another device using cold plasma is disclosed by WO 2007/031250 A1. The device according to this document is supposed to be used to disinfect wounds, more specifically the device comprises a plasma source with an outlet for dispensing the ionized gas onto an object. Several ionization electrodes are disposed within the ionization chamber for ionizing the gas and a predetermined ratio of the electrode-electrode distance on the one hand and the electrode-wall distance on the other hand.

One problem with such devices is that the skin interface area of the device may get contaminated and become dirty during treatment, for example when the device is used to treat a diseased skin, or if the device is used to treat skin of several different persons. Such devices may therefore cause hygiene concerns.

SUMMARY OF THE INVENTION

It is an object of the invention to provide a device for treating skin using non-thermal plasma which substantially alleviates or overcomes the problems mentioned above. In particular, at least in certain embodiments, the present invention sets out to provide a device for treating skin using non-thermal plasma in which the problem of contamination, in particular bacterial contamination, of the skin interface area is overcome or alleviated.

According to the present invention, there is provided a device for treating skin using non-thermal plasma, comprising:

a housing having a skin interface electrode for application to skin during treatment;

a generator for generating non-thermal plasma at the skin interface electrode; and an isolating element to isolate a region surrounding said skin interface electrode other than during treatment so that non-thermal plasma generated at the skin interface electrode within said region sterilises the skin interface electrode. The isolating element is configured to constrain non-thermal plasma generated by the device in a region surrounding the skin interface electrode. Therefore, the air surrounding the skin interface electrode gets saturated in ionized free particles and the skin interface electrode thereby gets sterilised.

The isolating element may be configured to cooperate with the housing. The isolating element may be configured to cooperate with the housing to form an airtight seal between the isolating element and the housing. In this way, the air captured around the skin interface electrode gets saturated in ionized free particles in a more efficient way, which enables a more efficient cleaning of the skin interface electrode.

One of the isolating element and the housing may comprise a projection and the other of the isolating element and the housing may comprise a recess, the projection being configured to engage the recess to secure the isolating element to the housing. This may ensure that the isolating element remains securely connected to the housing when the skin interface electrode is being sterilised.

The isolating element may comprise an isolating surface configured to face the skin interface electrode. The distance between the isolating surface and the skin interface electrode when the isolating element isolates the region surrounding the skin interface electrode may be at most 3 millimetres. The volume of the region surrounding the skin interface electrode and isolated by the isolating element is therefore minimised, and the ionized free particles are therefore generated proximate to the skin interface electrode. This provides the advantage of an enhanced sterilisation of the skin interface electrode.

The isolating element may be made from a rigid material, such as a thermoplastic polymer. This ensures that the skin interface electrode is protected against mechanical damage.

The isolating element may be a cap. Alternatively, the isolating element may be integrally formed as part of a dock to receive and support the housing. This enables a user to have the skin interface electrode cleaned while the device rests in the dock, for example between two treatments.

The device may comprise a power source to generate a low voltage electrical signal, and a transformer configured to change said low voltage electrical signal into a higher voltage electrical signal. The generator may be configured to receive said higher voltage electrical signal and generate non-thermal plasma at the skin interface electrode using said higher voltage electrical signal.

The generator may comprise a main electrode and a dielectric material disposed between the main electrode and the skin interface electrode. The main electrode may be connected to the transformer so that the higher voltage electrical signal is applied to the main electrode. The higher voltage electrical signal may be applied between the main electrode and the skin interface electrode. The skin interface electrode remains at a low or zero electrical potential. This ensures that, should a user accidentally touch the skin interface electrode, little or no current will pass thereby avoiding any injury.

According to a further aspect of the present invention, there is provided a method for sterilising a skin interface electrode of a device as described above, the method comprising:

positioning the isolating element relative to the housing so that the isolating element isolates a region surrounding said skin interface electrode; and activating the generator so that non-thermal plasma is generated at the skin interface electrode within said region and sterilises the skin interface electrode.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Referring to FIGS. 1 to 6, a skin treating device 10 according to a first embodiment of the present invention is shown. The device 10 is configured to treat skin using non-thermal plasma.

In the context of this application, the terms "non-thermal plasma", "cold plasma", "low-temperature plasma" or "non-equilibrium plasma" are equivalent. Non-thermal plasma has a temperature of less than about 40° C., i.e. a temperature tolerable to a person or user without causing injury or discomfort. In the context of this application, the terms "sterilise", "disinfect" and "decontaminate" mean that at least some of the microorganisms present on the surface of the skin are killed and/or rendered non-infectious. The terms "distal" and "proximal" herein respectively refer to as relatively closer to the skin to be treated and relatively further away from the skin to be treated.

In the present arrangement, the device 10 is configured to disinfect, sterilise or decontaminate a human or animal body surface, for example a part of the body in which bacteria are to be removed, such as an armpit, or a wound. The device 10 is configured to be hand-held. Therefore, the device 10 is of a mass, size and shape enabling a user to operate the device 10 for treating skin.

Figure 1:
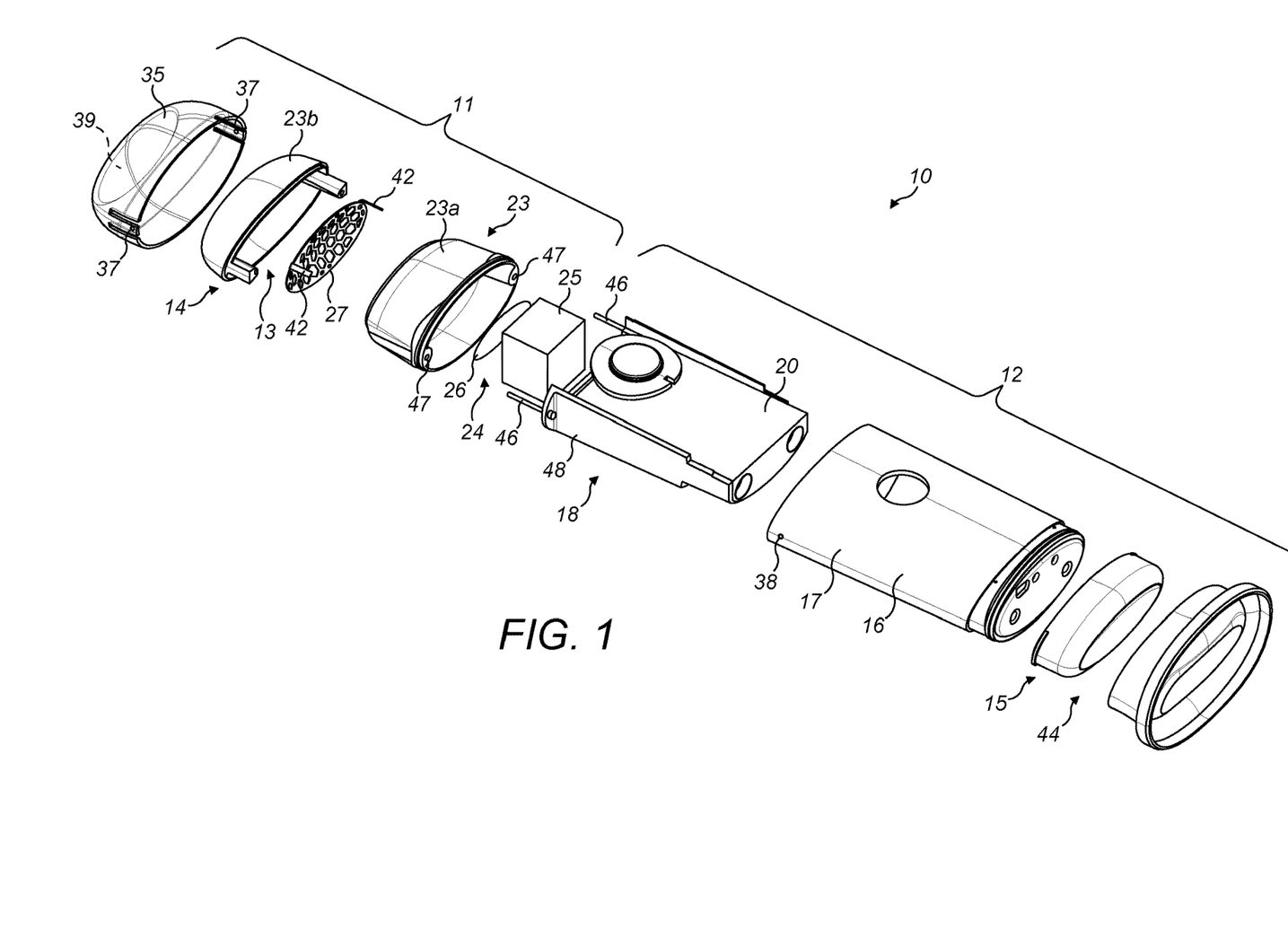
FIG. 1 shows an exploded view of a device for treating skin using non-thermal plasma according to a first embodiment of the present invention.
Figure 2:
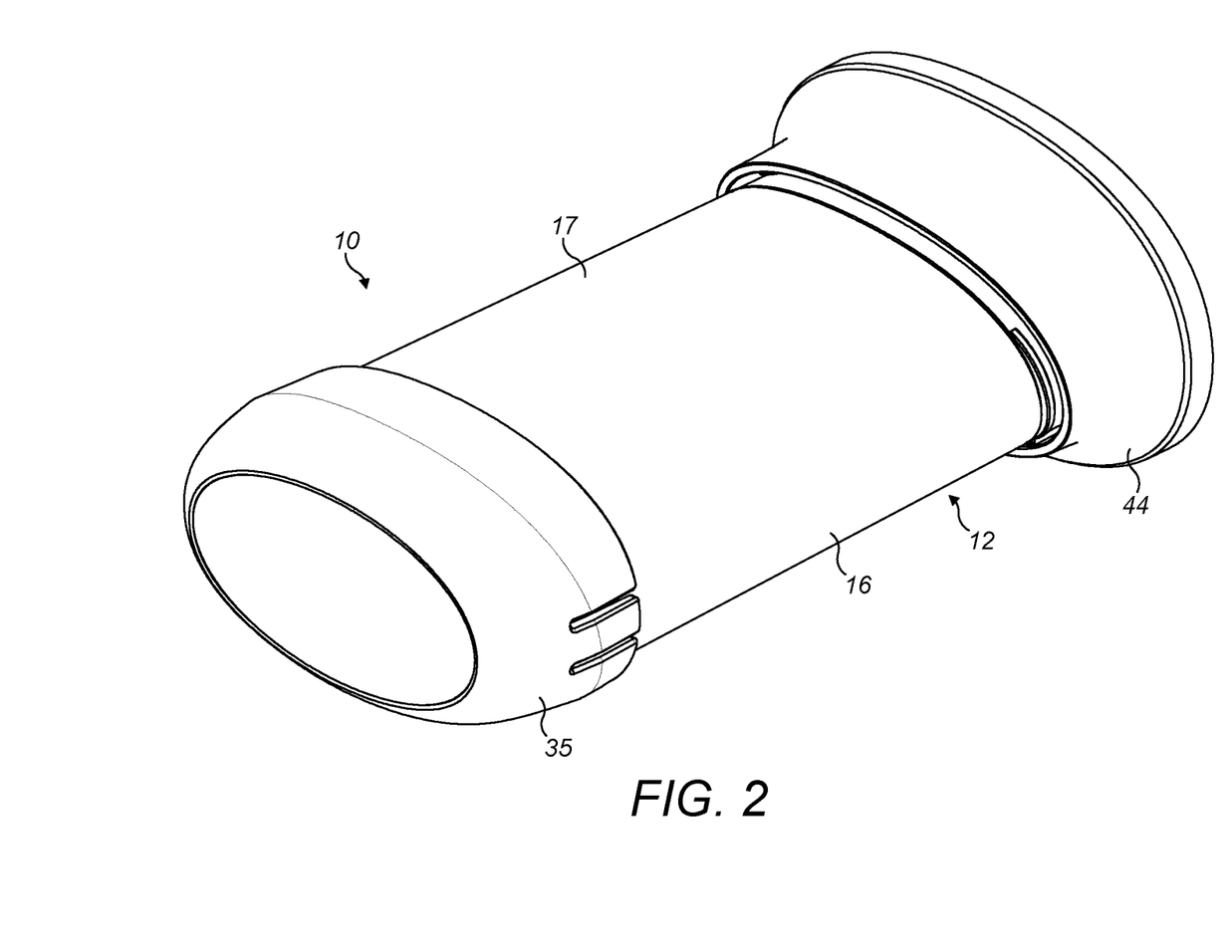
FIG. 2 shows a perspective view of the skin treating device of FIG. 1.

As shown in FIG. 1, the device 10 comprises an electrode head assembly 11 and a handle portion 12. The device 10 comprises a distal end 14 and a proximal end 15. The electrode head assembly 11 has a skin interface 13 located at the distal end 14 and suitable for application to skin during treatment.

The handle portion 12 comprises a housing 16 having a sidewall 17. The housing 16 accommodates the electrode head assembly 11 and a driving device 18 for driving the electrode head assembly 11.

Figure 4:
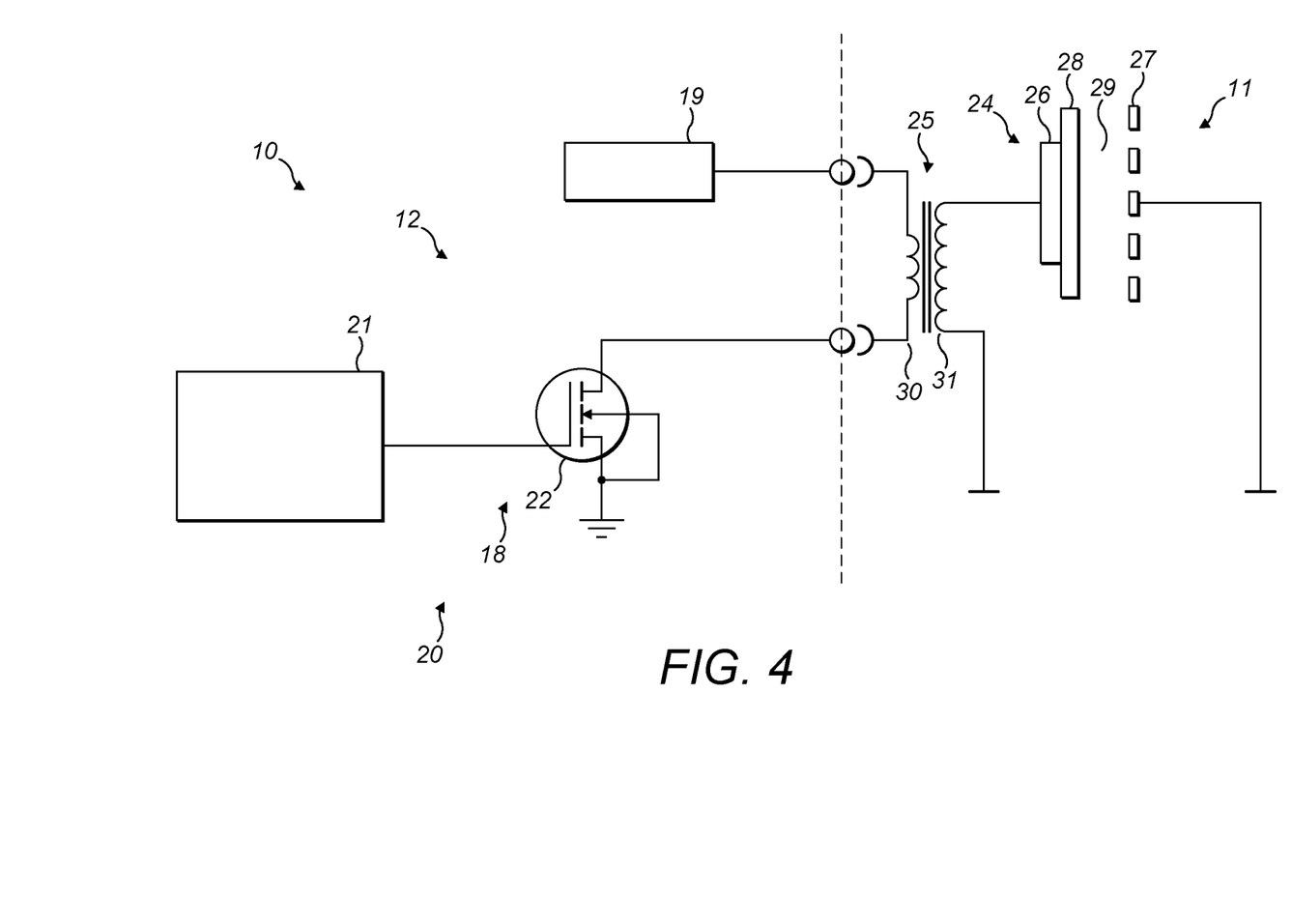
FIG. 4 shows a diagrammatic circuit diagram of the skin treating device of FIG. 1.

As shown in FIG. 4, the driving device 18 comprises a DC voltage source 19, such as a battery, and an electrical circuit 20. In the present arrangement, the electrical circuit 20 comprises a transistor-transistor logic (TTL) circuit 21 combined with a metal oxide semiconductor field effect transistor (MOSFET) 22. The output of the TTL circuit 21 is connected to the gate of the MOSFET 22. The driving device 18 is configured to generate a low voltage electrical signal. The voltage of the low voltage electrical signal generated by the driving device 18 ranges between about 15V and about 30V, and is in particular approximately equal to 24V. A switch (not shown) is provided on the sidewall 17 of the housing 16 to enable the user to switch on or switch off the driving device 18.

The electrode head assembly 11 comprises a body 23 having a first body portion 23a and a second body portion 23b and which accommodates a generator 24 for generating non-thermal plasma and a transformer 25 to supply a high voltage electrical signal to the generator 24.

The generator 24 comprises a main electrode 26 and a skin interface electrode 27, or counter-electrode. The main electrode 26 is located in the first body portion 23a. The main electrode 26 is in the form of a plate of conductive material. The skin interface electrode 27 is located at the skin interface 13 of the device 10 and is suitable for application to skin during treatment. The skin interface electrode 27 is mounted to the body 23. As visible in FIGS. 5D and 5E, the skin interface electrode 27 comprises a pair of lugs 42 which are inserted in corresponding slots 43 formed in the first body portion 23a. The lugs 42 tightly fit in the slots 43 such that the skin interface electrode 27 is securely mounted to the first body portion 23a. Each lug 42 comprises a protruding element 44 abutting against an inner surface 45 of the first body portion 23a such that the skin interface electrode 27 is prevented from being detached from the body 23. The skin interface electrode 27 is in the form of a grid or a mesh of conductive material. The shape of the grid or mesh of the skin interface electrode 27 can be adapted to control the flow of non-thermal plasma applied to the skin. A layer of dielectric material 28 is disposed along the main electrode 26 between the main electrode 26 and the skin interface electrode 27. The layer of dielectric material 28 is for example made of PTFE, polyoxymethylene, aluminium oxide or quartz. The layer of dielectric material 28 and the skin interface electrode 27 are arranged relative to each other in such a way that an air gap 29 locates between the layer of dielectric material 28 and the skin interface electrode 27.

The transformer 25 is configured to receive the low voltage electrical signal generated by the driving device 18, and is configured to transform the low voltage electrical signal received into a higher voltage electrical signal. Depending on the winding ratio of the transformer 25, the voltage of the low voltage electrical signal ranges between about 15V and about 30V and the voltage of the higher voltage electrical signal ranges between about 6 kV and about 7 kV. The voltage of the low voltage electrical signal is in particular approximately equal to 24V, and the voltage of the higher electrical signal is in particular approximately equal to 7 kV. The transformer 25 comprises a primary winding coil 30 and a secondary winding coil 31. The primary winding coil 30 is connected to the output of the driving device 18. The secondary winding coil 31 is connected to the main electrode 26 and the skin interface electrode 27 is maintained at a low or zero electrical potential, so that the higher voltage electrical signal is applied between the main electrode 26 and the skin interface electrode 27. As the skin interface electrode 27 is maintained at a low or zero electrical potential, little or no current will pass should the user accidentally touch the skin interface electrode, thereby avoiding any injury.

Figure 3:
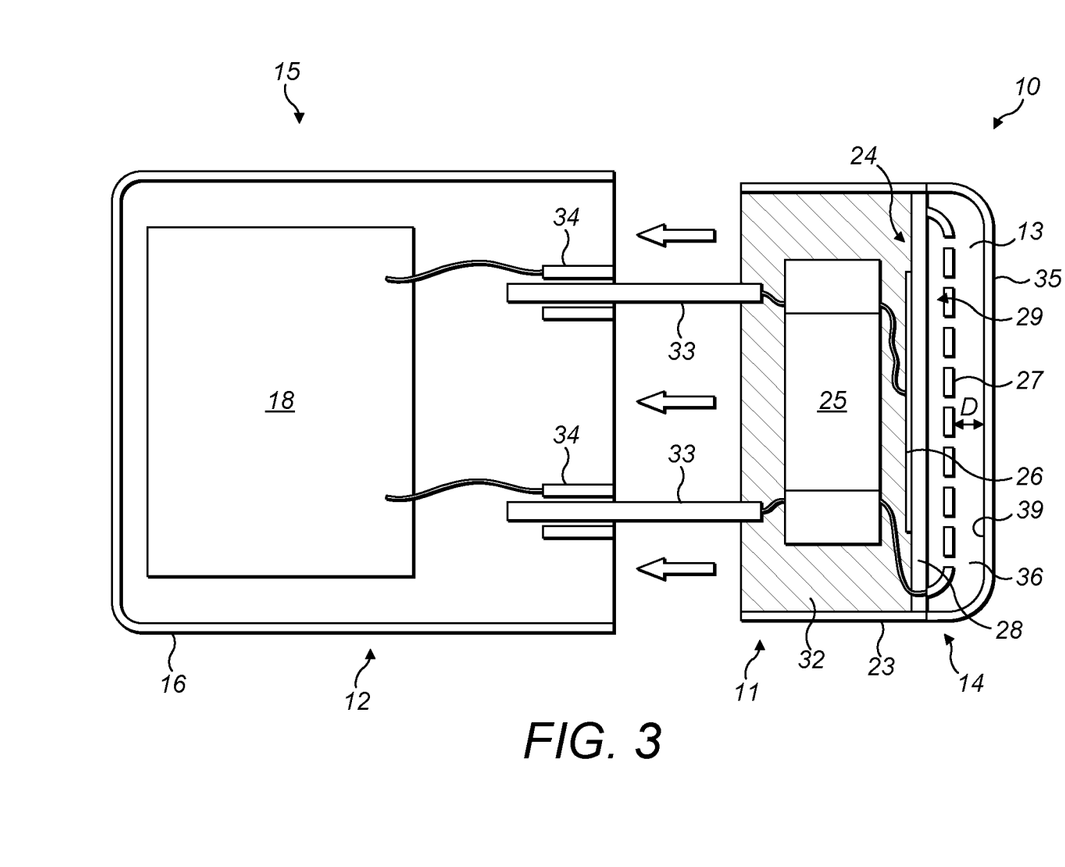
FIG. 3 shows a diagrammatic cross-sectional view of the skin treating device of FIG. 1.

As visible in FIG. 3, the transformer 25 and the main electrode 26 are embedded within a potting material 32 in the body 23. The potting material 32 is an electrically insulating material configured to electrically insulate the transformer 25 and the main electrode 26. The potting material 32 is hardenable and suitable for curing around the transformer 25 and the main electrode 26. For example, the potting material 32 is a thermosetting polymer, such as polyurethane, silicone, or epoxy resin. The potting material 32 provides electrical insulation from high electrical voltages generated within the electrode head assembly 11 during use, thereby enabling the electrode head assembly 11 to be at the same time compact and safe for the user.

The electrode head assembly 11 and the driving device 18 include cooperating elements to releasably mount the electrode head assembly 11 to the driving device 18 and electrically connect the driving device 18 to the transformer 25. The cooperating elements are in the form of a pair of plugs 33 and a pair of corresponding sockets 34. The plugs 33 are part of the electrode head assembly 11 and are electrically connected to the primary winding coil 30 of the transformer 25. The sockets 34 are arranged in the driving device 18 and electrically connected to the driving device 18. Each plug 33 is configured to respectively engage with one of the sockets 34 to releasably mount the electrode head assembly 11 to the driving device 18. When engaged with each other, the pairs of plugs 33 and sockets 34 electrically connect the driving device 18 to the primary winding coil 30 so that the low voltage electrical signal generated by the driving device 18 is transmitted to the primary winding coil 30. The device 10 is therefore configured such that no high voltage electrical signal is transmitted through the plugs 33, i.e. through the interface between the driving device 18 and the electrode head assembly 11. A user can therefore detach the electrode head assembly 11 from the driving device 18 without any risks.

Figure 5A:
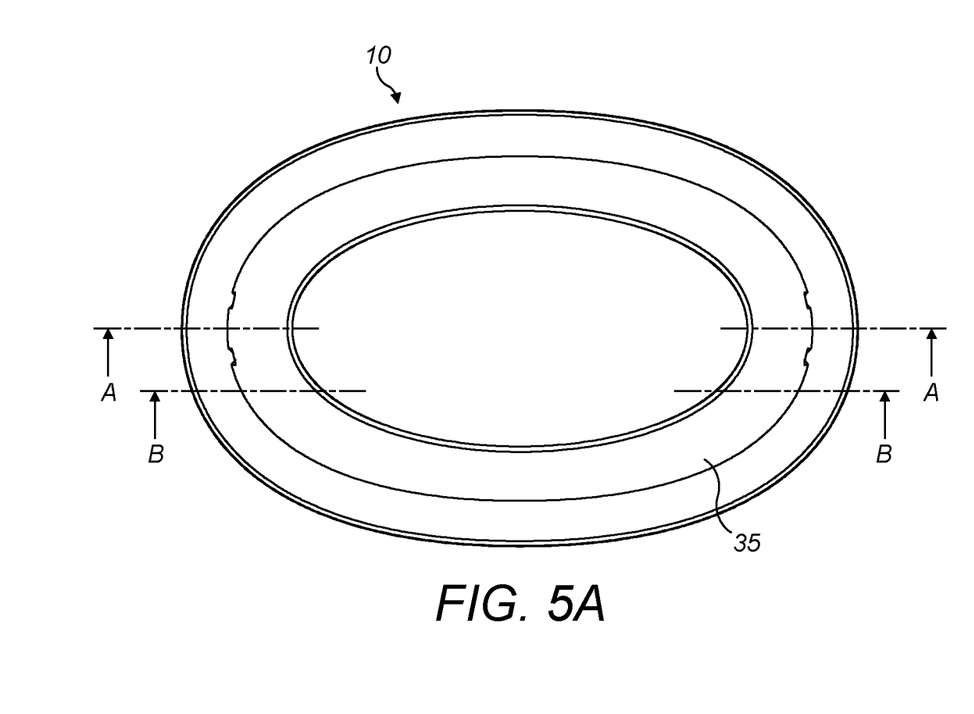
FIG. 5A shows a top view of the skin treating device of FIG. 1.
Figure 5B:
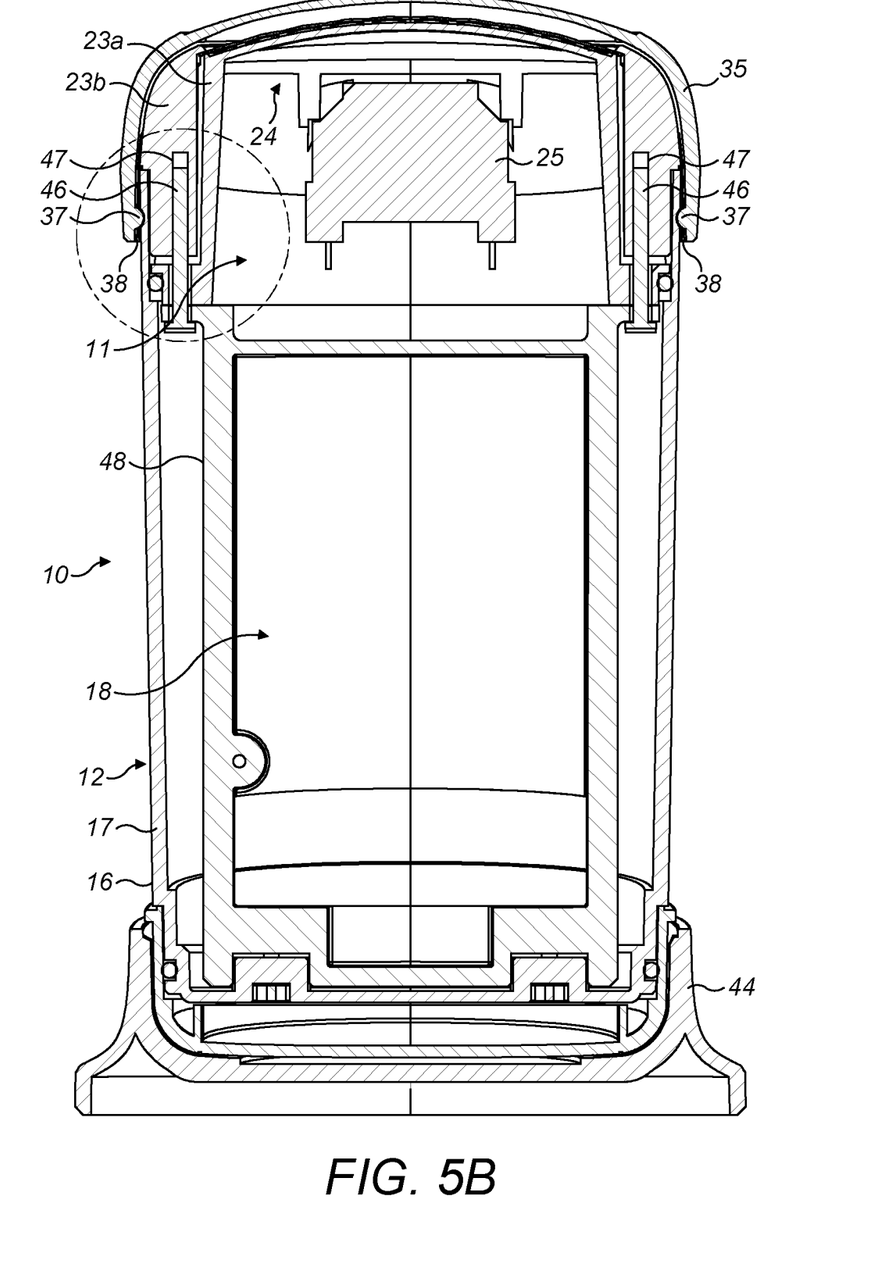
FIG. 5B shows a cross-sectional view of the skin treating device of FIG. 1 taken along the line A-A shown in FIG. 5A.
Figure 5C:
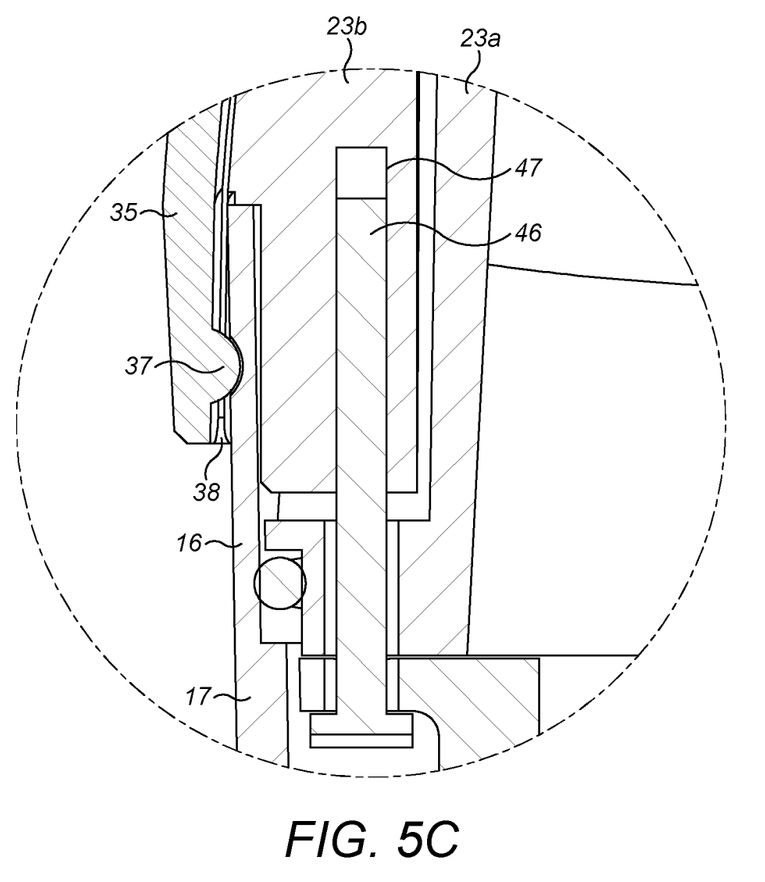
FIG. 5C shows an enlarged view of a detail of the skin treating device of FIG. 5B.
Figure 5D:
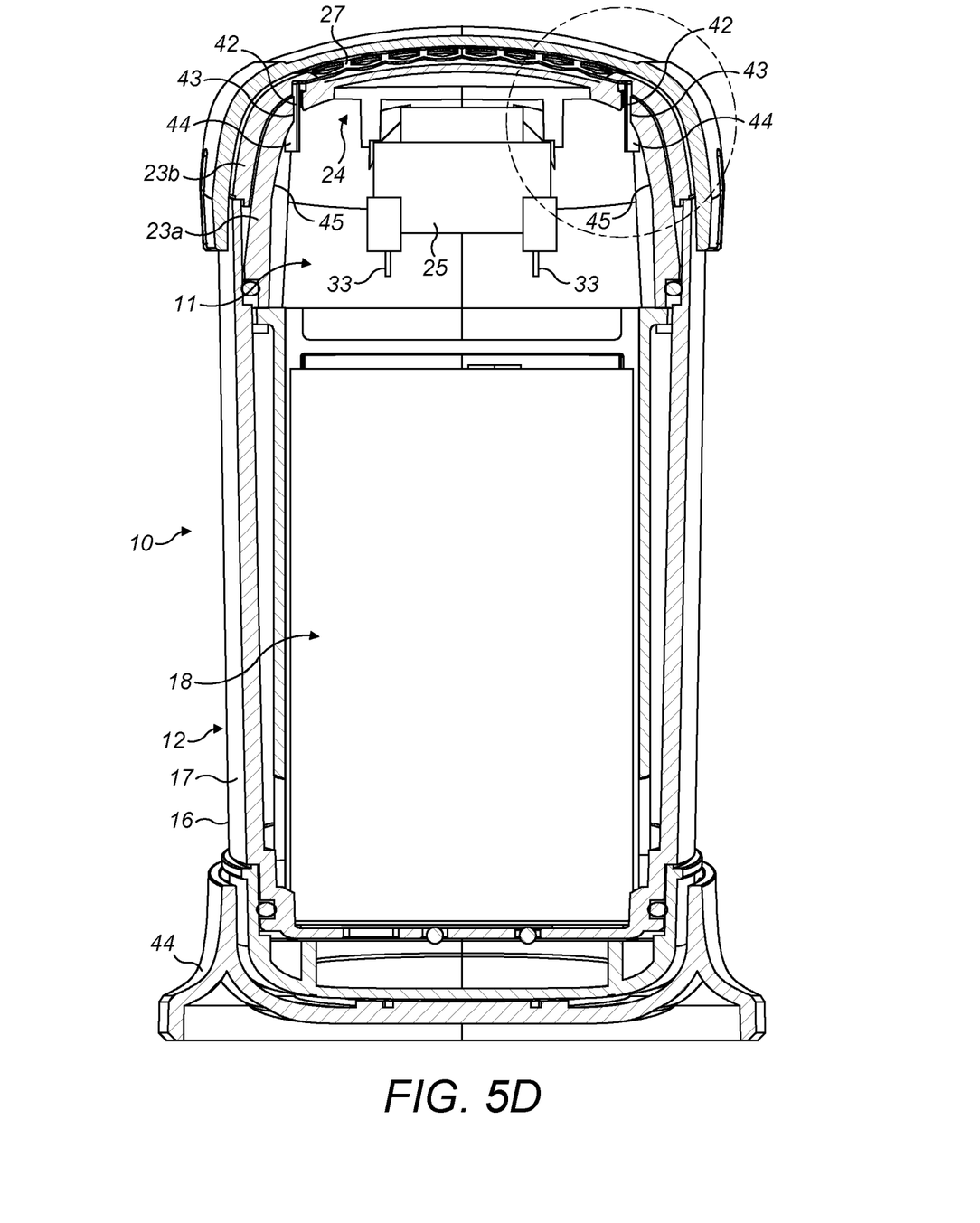
FIG. 5D shows a cross-sectional view of the skin treating device of FIG. 1 taken along the line B-B shown in FIG. 5A.
Figure 5E:
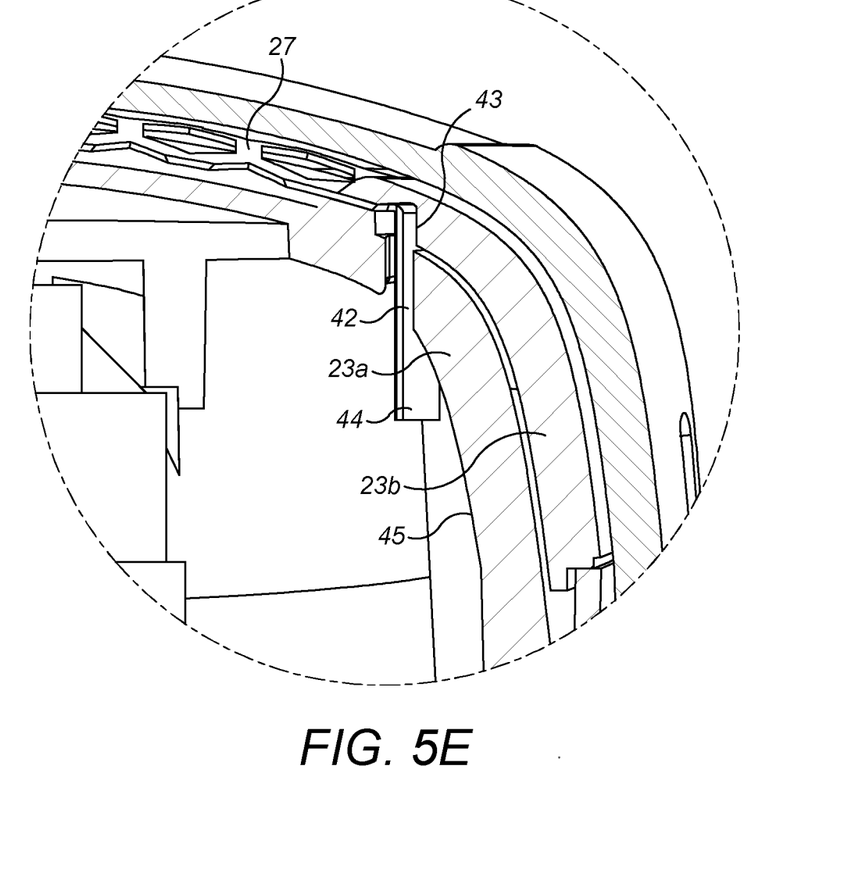
FIG. 5E shows an enlarged view of a detail of the skin treating device of FIG. 5D.

The device 10 comprises additional securing elements in the form of a pair of screws 46 and a pair of corresponding holes 47. As shown in FIGS. 1 and 5B, the screws 46 are attached to a sidewall 48 of the driving device 18 and the holes 47 are arranged in the body 23. Each screw 46 is configured to respectively engage with one of the holes 47 to additionally secure the electrode head assembly 11 to the driving device 18.

Figure 6:
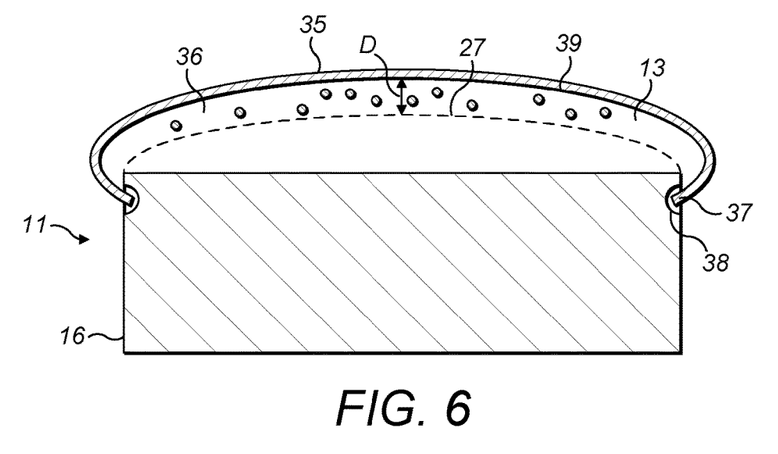
FIG. 6 shows a partial diagrammatic cross-sectional view of the electrode head assembly of the skin treating device of FIG. 1.

As visible in FIG. 6, an isolating element 35 is provided at the skin interface 13 of the device 10. In the present embodiment, the isolating element 35 is in the form of a cap 35. The cap 35 is configured to cooperate with the housing 16. As visible in FIGS. 5B and 5C, the cap 35 comprises a pair of projections 37 which are configured to engage in corresponding recesses 38 formed in the sidewall 17 of the housing 16 such that an airtight seal is formed between the cap 35 and the housing 16. The cap 35 is configured to be positioned in an isolating position, in which the cap 35 isolates a region surrounding the skin interface electrode 27 to form a closed chamber 36 around the skin interface electrode 27.

When the cap 35 is in the isolating position and when non-thermal plasma is generated at the skin interface electrode 27, non-thermal plasma is contained within the closed chamber 36 about the skin interface electrode 27. In this way, the air captured in the closed chamber 36 and surrounding the skin interface electrode 27 gets saturated in ionized free particles, and the skin interface electrode 27 thereby gets cleaned and disinfected.

The cap 35 comprises an isolating surface 39 which faces the skin interface electrode 27 when the cap 35 is in the isolating position. In the isolating position, the distance D between the isolating surface 39 and the skin interface electrode 27 is at most 3 millimetres, and preferably ranges between about 0.2 millimetre and about 1 millimetre. This allows minimizing the volume of the closed chamber 36 formed around the skin interface electrode 27. In this way, the air captured in the closed chamber 36 gets more efficiently saturated in ionized free particles and an enhanced cleaning of the skin interface electrode 27 is therefore enabled.

The cap 35 is made from a rigid material such as a thermoplastic polymer. For example, the cap 35 is made from acrylonitrile butadiene styrene or polycarbonate. It will be noted that any other kind of material suitable for protecting the skin interface electrode 27 against mechanical damage can be used.

The device 10 may additionally comprise a stand 44 configured to stabilise the device 10 when the device 10 is placed in an upright position, for example on a table. The stand 44 receives the proximal end 15 of the device 10.

The operation of the skin treating device 10 in accordance with the first embodiment of the present invention will now be described.

Initially, the transformer 25 is electrically connected to the driving device 18 and the electrode head assembly 11 is mounted to the driving device 18 via the plugs and sockets 33, 34. The electrode head assembly 11 is additionally secured to the driving device 18 by fixing the screws 46 in the holes 47. In use, the driving device 18 is switched on by a user by means of the switch, and the skin interface 13 of the device 10 is positioned against or close to an area of skin to be sterilized, for example a wound. Alternatively, or more in general, the device 10 is positioned against or close to a part of the body in which bacteria are to be removed, such as an armpit. Once the driving device 18 is switched on, the driving device 18 generates a low voltage electrical signal which is transmitted to the primary winding coil 30 of the transformer 25 via the plugs and sockets 33, 34. The transformer 25 changes the low voltage electrical signal into a higher voltage electrical signal which is applied between the main electrode 26 and the skin interface electrode 27. This creates electrical discharges which ionize air located between the main electrode 26 and the skin interface electrode 27 and generate non-thermal plasma at the skin interface electrode 27. The generated non-thermal plasma diffuses onto the skin, thereby disinfecting the skin.

During treatment of the skin, the skin interface electrode 27 is positioned close to or directly against the part of the body in which bacteria are to be removed, and may therefore get contaminated. Accordingly, after treatment, the user may want to clean the skin interface electrode 27 before reusing the device 10. To this effect, the user positions the cap 35 in the isolating position so that the cap 35 is snapped on the housing 16 and forms the closed chamber 36 around the skin interface electrode 27. Then, the user switches the driving device 18 on by means of the switch. Non-thermal plasma is generated at the skin interface electrode 27 and is contained within the closed chamber 36 about the skin interface electrode 27. Therefore, the air captured in the closed chamber 36 and surrounding the skin interface electrode 27 gets saturated with ionized free particles, and the skin interface electrode 27 thereby gets cleaned and disinfected.

Alternatively, or in addition, the user may want to change of electrode head assembly 11, of may want to wash the electrode head assembly 11. To this effect, the user detaches the cap 35 from the housing 16, and detaches the electrode head assembly 11 from the driving device 18 by removing the plugs 33 from the sockets 34 and the screws 46 from the holes 47. As no high voltage electrical signal is transmitted through the plugs and sockets 33, 34 between the driving device 18 and the electrode head assembly 11, the electrode head assembly 11 can be removed from the driving device 18 without risks for the user.

Figure 7A:
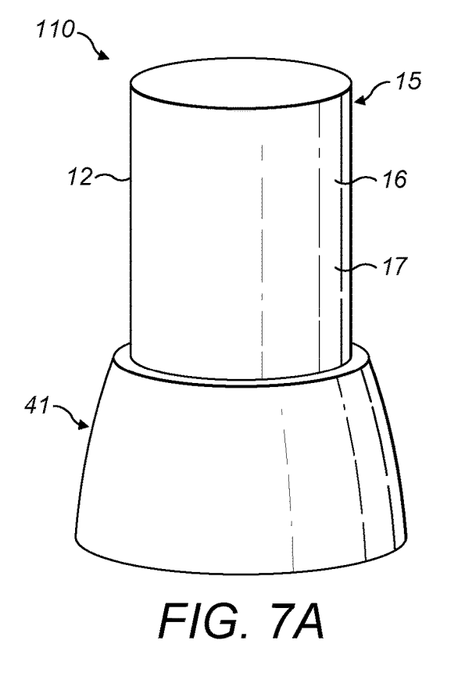
FIG. 7A shows a diagrammatic perspective view of a device for treating skin using non-thermal plasma according to a second embodiment of the present invention.
Figure 7B:
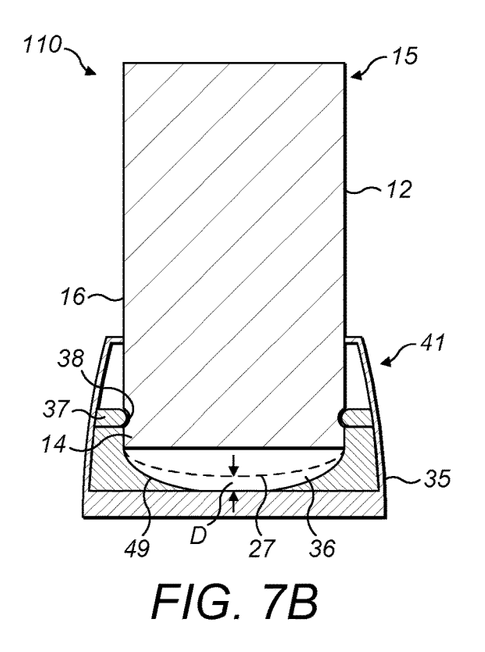
FIG. 7B shows a diagrammatic cross-sectional view of the skin treating device of FIG. 7A.

A second embodiment 110 of the skin treating device according to the present invention is shown in FIGS. 7A and 7B. The second embodiment corresponds closely to the first embodiment and like reference numerals have been used for like components.

As shown in FIG. 7A, the isolating element is in the form of a wall 49 integrally formed as part of a dock 41 to receive and support the device 110. The dock 41 is configured to receive the distal end 14 of the device 110. When the device 110 is placed in the dock 41, the wall 49 cooperates with the housing 16 to form an airtight seal between the dock 41 and the housing 16. As shown in FIG. 7B, the wall 49 comprises a projection 37 which is configured to engage in a corresponding recess 38 formed in the housing 16 to form an airtight seal between the housing 16 and the dock 41 and to form the closed chamber 36 around the skin interface electrode 27.

It will be appreciated that the operation of the skin treating device 110 according to the second embodiment is unchanged from that of the first embodiment. However, in the second embodiment, when the user wants to sterilise the skin interface electrode 27, the user positions the distal end 14 of the device 110 in the dock 41 so that the projection 37 of the wall 49 engages the recess 38 in the housing 16 to form the closed chamber 36 around the skin interface electrode 27. The driving device 18 is then switched on and non-thermal plasma is generated at the skin interface electrode 27 within the closed chamber 36 so that the skin interface electrode 27 gets sterilised.

While embodiments of the invention have been illustrated and described in detail in the drawings and foregoing description, such illustration and description are to be considered illustrative or exemplary and not restrictive, and the invention not limited to these embodiments.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A device for treating skin using non-thermal plasma, the device comprising:
   a housing having a skin interface electrode for application to skin during treatment;
   a generator for generating non-thermal plasma at the skin interface electrode; and
   an isolating element to isolate an airtight region surrounding said skin interface electrode other than during treatment so that non-thermal plasma generated at the skin interface electrode within said airtight region sterilises the skin interface electrode;
   wherein the isolating element is integrally formed as part of a dock to receive and support the housing.

2. The device according to claim 1, wherein the isolating element is configured to cooperate with the housing.

3. The device according to claim 2, wherein the isolating element is configured to cooperate with the housing to form an airtight seal between the isolating element and the housing.

4. The device according to claim 2,
   wherein one of the isolating element and the housing includes a projection; and
   wherein an other of the isolating element and the housing includes a recess, the projection being configured to engage the recess to secure the isolating element to the housing.

5. The device according to claim 1,
   wherein the isolating element comprises an isolating surface configured to face the skin interface electrode, and
   wherein the distance (D) between the isolating surface and the skin interface electrode when the isolating element isolates the airtight region surrounding the skin interface electrode is at most 3 millimetres.

6. The device according to claim 1, wherein the isolating element is made from a rigid material.

7. The device according to claim 1, wherein the isolating element is a cap.

8. The device according to claim 1, further comprising:
   a power source to generate a low voltage electrical signal;
   a transformer configured to change said low voltage electrical signal into a higher voltage electrical signal; and wherein the generator is configured to receive said higher voltage electrical signal and to generate the non-thermal plasma at the skin interface electrode using said higher voltage electrical signal.

9. The device according to claim 8,
wherein the generator includes a main electrode and a dielectric material disposed between the main electrode and the skin interface electrode; and
wherein the main electrode is connected to the transformer so that the higher voltage electrical signal is applied to the main electrode.

10. A method for sterilising a skin interface electrode of a device including a housing having a skin interface electrode for application to skin during treatment, a generator for generating non-thermal plasma at the skin interface electrode, and an isolating element to isolate an airtight region surrounding said skin interface electrode other than during treatment so that non-thermal plasma generated at the skin interface electrode within said airtight region sterilises the skin interface electrode,
the method comprising:
positioning the isolating element relative to the housing so that the isolating element isolates the airtight region surrounding said skin interface electrode; and
activating the generator so that a first non-thermal plasma is generated at the skin interface electrode within said airtight region and sterilises the skin interface electrode.

11. The method of claim 10, further comprising:
repositioning the isolating element relative to the housing so that said skin interface electrode is positioned directly against skin; and
reactivating the generator so that a second non-thermal plasma is generated at the skin interface electrode to treat the skin.

12. A device for treating skin using non-thermal plasma, comprising:
a skin interface electrode for application to skin during treatment;
a generator for generating non-thermal plasma at the skin interface electrode;
a housing accommodating the skin interface electrode and the generator; and
an isolating element cooperative with the housing to isolate an airtight region surrounding said skin interface electrode so that non-thermal plasma generated at the skin interface electrode within said airtight region sterilises the skin interface electrode;
wherein the isolating element is integrally formed as part of a dock to receive and support the housing.

13. The device according to claim 12,
wherein one of the isolating element and the housing includes a projection; and
wherein an other of the isolating element and the housing includes a recess, the projection being configured to engage the recess to secure the isolating element to the housing.

14. The device according to claim 12,
wherein the isolating element comprises an isolating surface configured to face the skin interface electrode, and
wherein the distance (D) between the isolating surface and the skin interface electrode when the isolating element isolates the airtight region surrounding the skin interface electrode is at most 3 millimetres.

15. The device according to claim 12, wherein the isolating element is made from a rigid material.

16. The device according to claim 12, wherein the isolating element is a cap.

17. The device according to claim 12, further comprising:
a power source to generate a low voltage electrical signal;
a transformer configured to change said low voltage electrical signal into a higher voltage electrical signal;
wherein the housing further accommodates the power source and the transformer; and
wherein the generator is configured to receive said higher voltage electrical signal and to generate the non-thermal plasma at the skin interface electrode using said higher voltage electrical signal.

18. The device according to claim 17,
wherein the generator includes a main electrode and a dielectric material disposed between the main electrode and the skin interface electrode; and
wherein the main electrode is connected to the transformer so that the higher voltage electrical signal is applied to the main electrode.

* * * * *